(12) United States Patent
Uckun

(10) Patent No.: US 6,958,359 B1
(45) Date of Patent: Oct. 25, 2005

(54) VANADIUM COMPOUNDS AS ANTI-ANGIOGENIC AGENTS

(75) Inventor: Fatih M. Uckun, White Bear Lake, MN (US)

(73) Assignee: Parker Hughes Institute, Roseville, MN (US)

( * ) Notice: Subject to any disclaimer, the term of this patent is extended or adjusted under 35 U.S.C. 154(b) by 0 days.

(21) Appl. No.: 09/713,780

(22) Filed: Nov. 15, 2000

(51) Int. Cl.$^7$ .................. A61K 31/28; A61K 33/24; A61K 31/555

(52) U.S. Cl. .............. 514/492; 514/184; 514/185; 514/186; 514/188; 514/334; 514/822; 514/824; 514/863; 514/866; 514/883; 514/908; 514/912; 514/954; 424/646

(58) Field of Search .................. 424/646; 514/184–186, 514/188, 492, 824, 863, 883, 908, 912, 954, 822, 866, 334

(56) References Cited

U.S. PATENT DOCUMENTS

| | | | |
|---|---|---|---|
| 4,559,157 A | | 12/1985 | Smith et al. |
| 4,608,392 A | | 8/1986 | Jacquet et al. |
| 4,820,508 A | | 4/1989 | Wortzman |
| 4,938,949 A | | 7/1990 | Borch et al. |
| 4,992,478 A | | 2/1991 | Geria |
| 5,648,382 A | * | 7/1997 | Billington et al. .......... 514/475 |
| 5,871,779 A | * | 2/1999 | Cruz .......................... 424/646 |

FOREIGN PATENT DOCUMENTS

| | | |
|---|---|---|
| WO | WO 99/36063 | 7/1999 |
| WO | WO 00/27389 | 5/2000 |
| WO | WO 00/35930 | 6/2000 |

OTHER PUBLICATIONS

Doyle et al., *Inorg. Chem.,* 7: 2479–2484, 1968.
Mullins et al., 1994, *Arterioscler. Thromb.,* 14: 1047–1055.
Wilkinson et al., *J. Am. Chem. Soc.,* 76: 4281–4284, 1954.
Auerbach et al, *Developmental Biology*, 41:39, 1974.
Benyumov et al, *Rus. J. Dev. Biol.,* 26(2):132, 1995
Cahill et al, *Nature*, 392: 300–303, 1998.
Evans, *J Chem Soc*, 2003, 1959.
Folkman, *Ann Surg*, 175:409, 1972.
Folkman et al, *Science*, 235:442, 1985.
Folkman, *Nat. Med.,* 1:27, 1995.
Ghosh et al, *Clinc Canc Res,* 6:1536, 2000.
Gimbrane et al, *J Exp Med,* 136:261, 1972.
Gorbsky et al, *Bioessays,* 19: 193–197, 1997.
Hardwick, K. G., *Trends Genet.,* 14: 1–4, 1998.
Hoyt et al, *Cell,* 66: 507–517, 1991.
Hyde, Rev Sci Instrum, 43: 629, 1972.
Kimmel et al, *Dev. Dynam.,* 203:253, 1995.
Kopf–Maier, et al, *J Cancer Res. Clin. Onccol.,* 106: 44–52, 1983.
Landzberg, et. al., 1997, *Prog. Cardiovascular Diseases*, 39:361–298.
Li et al, *Cell*, 66: 519–531, 1991.
Mullins et al., 1994, *Arterioscler. Thromb.,* 14:1047–1055.
Nguyen et al, *Microvascular Research,* 47:31, 1994.
Sakurai, et. al., *BBRC,* 206: 133, 1995.
Taylar et al, *Nature,* 297:307, 1982.
Ueda et al., 1995, *Coron. Artery Dis.,* 6:71–81.
Vaitkus, P.T., 1995, *Coron. Atery Dis.,* 6:429–439.
Westerfield, *The Zebrafish Book,* 1993, 2d Edition Univ. of Oregon Press, Eugene.
Mullins et al., 1994, *Arterioscler. Thromb.,* 14:1047–1055.

* cited by examiner

*Primary Examiner*—John Pak
(74) *Attorney, Agent, or Firm*—Merchant & Gould P.C.

(57) ABSTRACT

Vanadium compounds for inhibiting angiogenesis useful for treating or preventing diabetic retinopathy, hemangiomas, cancers with abnormal blood vessel supply, restenosis following vascular injury, and the like.

39 Claims, No Drawings

VANADIUM COMPOUNDS AS ANTI-ANGIOGENIC AGENTS

BACKGROUND OF THE INVENTION

Tissue growth is intimately associated with blood supply. Non-vascularized tissue is limited in size, often being smaller than one to two millimeters in diameter or thickness. Therefore, inhibiting blood supply to tissue represents one target point for limiting tissue growth and possibly tissue viability.

The ability to inhibit blood supply has been shown to play a pivotal role in the progression, invasive and metastatic growth of malignant tumors (Folman, *Nat Med*, 1:27, 1995; Folkman et al, *Science*, 235:442, 1985; Gimbrane et al, *J Exp Med*, 136:261, 1972). Further, inhibition of angiogenesis new vessel formation), has been shown to result in tumor dormancy or regression and to prevent metastasis (Folkman, *Ann Surg*, 175:409, 1972; Taylar et al, *Nature*, 297:307, 1982).

Another possible target for inhibiting tissue growth is by inhibiting cell proliferation. All proliferating eucaryotic cells must undergo mitosis before separating into two new cells. Mitosis is a process in which the parent or replicating cell undergoes a series of molecular events that results in the formation of two nuclei in the place of one.

The polar mitotic spindle is critical to the separation of the replicated chromosomes and formation of the two nuclei in the mitotic process. For mitosis to proceed normally, cells must properly form a bipolar mitotic spindle with bivalent chromosomes properly attached to each pole of the spindle (Gorbsky et al, *Bioessays*, 19: 193–197, 1997; Hardwick, K. G., *Trends Genet.*, 14: 1–4, 1998). Cells which do not form a correct mitotic spindle arrest indefinitely in the metaphase stage of mitosis or progress into apoptosis. Several proteins identified in yeast and mammals have been implicated in this process, including MAD1 (mitotic arrest deficient), MAD2, and MAD3 (Li et al, *Cell*, 66: 519–531, 1991 (*published erratum appears in Cell*, 79(2), following p388)), BUB1 (budding uninhibited by benzimidazole), BUB2 and BUB3 (Hoyt et al, *Cell*, 66: 507–517, 1991). Mammalian counterparts for these proteins include HsMAD2 (Li et al, Supra and hBUB1 (Cahill et al, *Nature*, 392: 300–303, 1998).

Revascularization of obstructed coronary arteries by percutaneous transluminal coronary angioplasty (PTCA) has become an integral component of front-line treatment programs for patients with ischermic heart disease (Vaitkus, P. T., 1995, *Coron. Atery Dis.*, 6:429–439). Although acute complications of PTCA have markedly declined with optimized use of anticoagulants, antispasmodic agents, and intravascular stents, the incidence of coronary artery restenosis has remained at 30%–50% and represents the major obstacle to a more successful outcome of PTCA (Landzberg, et. al., 1997, *Prog. Cardiovascular Diseases*, 39:361–298). Therefore, the development of effective strategies for restenosis prophylaxis has become a focal point for translational cardiovascular research.

The pathogenesis of restenosis has been compared to an exaggerated wound healing response with migration of smooth muscle cells from the media to the intima of the revascularized coronary artery where they proliferate and cause an obstructive neointimal hyperplasia (Ueda et al., 1995, *Coron. Artery Dis*, 6:71–81). Many factors contribute to the development of restenosis, including vascular injury, platelet aggregation, procedural factors, inflammation, and mitogenic stimulation of migration and proliferation of smooth muscle cells. The relative contribution of any one of these factors remains unclear.

Pharmacological approaches to prevent restenosis include antiplatelet and antithrombotic agents, anti-inflammatory drugs, growth factor antagonists, vasodilators, antiproliferatives, antineoplastics, photochemotherapy, and lipid lowering agents. Some growth factor antagonists have also been studied for effects on restenosis.

Inhibition of vascular smooth muscle cell proliferation by a platelet derived growth factor (PDGF)antagonist has generated promising results in preclinical as well as early clinical studies, thereby confirming the biologic importance of vascular smooth muscle cells in the pathophysiology of restenosis (Mullins et al., 1994, *Arterioscler. Thromb.*, 14:1047–1055).

Considerable efforts are underway to develop new anti-angiogenic and anti-mitotic agents for use as therapies in the treatment of tumor growth and spread. Accordingly, there is a need for the analysis of novel, effective anti-angiogenic and anti-mitotic agents that target tumor growth.

Vanadocene dichloride (VDC) has been shown to arrest tumor cells growth (Kopf-Maier, et al, *J Cancer Res. Clin. Onccol.*, 106: 44–52, 1983). The oxovanadium compound, $VO(Phen)H_2O)_2](SO_4)$, has been shown to be an active agent against pharyngonasal cancer as determined by a single assay (Sakurai, et. al, *BBRC*, 206: 133, 1995). Vanadium compounds, including vanadocenes, have also been demonstrated to induce apoptosis in cancer cells (Uckun et al., WO 00/35930).

Against this backdrop the present invention has been developed.

SUMMARY OF THE INVENTION

It has been now found that vanadium compounds, for example, vanadocenes and oxovanadium compounds, are poent agents for inhibiting angiogenesis. In particular, the vanadium compounds have been found to exhibit dual function inhibiting both angiogenesis and mitosis. Pharmaceutical compositions containing these vanadium compounds are thus useful in methods to inhibit angiogenesis and mitosis, for example, in the treatment diabetic retinopathy, hemangiomas, cancers with abnormal blood vessel supply, restenosis following vascular injury, and the like.

DETAILED DESCRIPTION OF THE PREFERRED EMBODIMENT

The present invention relates to vanadium compounds, including, for example, vanadium cyclopentadienyl complexes (vanadocenes), such as vandocene acetylacetonate (VDacac) and oxovanadium compounds, and the finding that these vanadium compounds have potent anti-angiogenic and anti-mitotic activities.

Vanadium is a physiologically essential element that can be found in both anionic and cationic forms with oxidation states ranging from −3 to +5 (I–V). This versatility provides unique properties to vanadium complexes. In particular, the catonic form of vanadium complexes having an oxidation state of +4 (IV) has been shown to function as a modulator of cellular redox potential, regulate enzymatic phosphorylation, and exert pleiotropic effects in multiple biological systems by catalyzing the generation of reactive oxygen species (ROS). Besides the ability of vanadium metal to assume various oxidation states, its coordination chemistry also plays a key role in its interactions with various biomolecules. In particular, it is demonstrated herein that vanadium compounds, such as vanadium cyclopentadienyl complexes, oxovanadium complexes, or derivatives thereof, exhibit anti-angiogenic and anti-mitotic properties.

DEFINITIONS

The following terms and phrases as used herein have the noted definitions, unless otherwise described:

"Halo" is fluoro, chloro, bromo, or iodo.

"Alkyl", "alkoxy", etc. denote both straight and branched hydrocarbon groups; but reference to an individual radical such as "propyl" embraces only the straight chain radical, a branched chain isomer such as "isopropyl" is specifically referenced.

"Organometallic compound" is an organic compound comprised of a metal attached directly to carbon (R-M).

"Coordination compound" is a compound formed by the union of a central metal atom or ion with ions or molecules called ligands or complexing agents.

"Ligand" or a "complexing agent" is a molecule, ion or atom that is attached to the central metal atom or ion of a coordination compound.

"Monodentate ligand" is a ligand having a single donor atom coordinated to the central metal atom or ion.

"Bidentate ligand" is a ligand having two donor atoms coordinated to the same central metal atom or ion.

"Vanadocene" is a compound having a central vanadium metal ion coordinated with at least two cyclopentadiene groups.

It will be appreciated that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein. Methods to prepare optically active forms are known, for example, by resolution of the racemic form by recrystallization techniques, by synthesis from optically-active starting materials, by chiral synthesis, or by chromatographic separation using a chiral stationary phase. Methods for determining anti-mitotic and anti-meiotic activity of a compound are known, for example, using the standard tests described herein, or other known tests.

Specific values listed below for radicals, substituents, and ranges, are for illustration only; they do not exclude other defined values or other values within defined ranges for the radicals and substituents.

For example, $(C_1-C_6)$ alkyl can be methyl, ethyl, propyl, isopropyl, butyl, iso-butyl, sec-butyl, pentyl, 3-pentyl, or hexyl; $(C_1-C_3)$ alkyl can be methyl, ethyl or propyl; halo $(C_1-C_3)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; $(C_1-C_3)$alkoxy can be methoxy, ethoxy, or propoxy; and $(C_2-C_6)$alkanoyloxy can be acetoxy, propanoyloxy, butanoyloxy, isobutanoyloxy, pentanoyloxy, or hexanoyloxy.

The following glossary of vanadium compounds is provided to clarify terms used throughout the specification and provides a listing of exemplary vanadium compounds useful in the method invention:

Group A: Vanadocene dihalides
VDC Vanadocene dichloride ($Cp_2VCl_2$)
VMDC Bis(methyl cyclopentadienyl)vanadium dichloride [$(MeCp)_2VCl_2$]
VDB Vanadocene dibromide ($Cp_2VBr_2$)
VDI Vanadocene diiodide ($Cp_2VI_2$)
Group B: Vanadocene di-pseudohalides
VDA Vanadocene diazide [$Cp_2V(N_3)_2$]
VDCN Vanadocene dicyanide ($Cp_2V(CN)_2$)
VDOCN Vanadocene dioxycyanate ($Cp_2V(OCN)_2$)
VDSCN Vanadocene dithiocyanate ($Cp_2V(SCN)_2$)
VDSeCN Vanadocene diselenocyanate ($VCp_2(SeCN)_2$)
Group C: Vanadocene disubstituted derivatives
VDT Vanadocene ditriflate ($Cp_2V(O_3SCF_3)_2$)
VDCO Vanadocene monochloro oxycyanate ($Cp_2V(OCN)(Cl)$)
VDFe Vanadocene monoacetonitrilomonochloro tetrachloro ferrate ($Cp_2VClNCCH_3$)$FeCl_4$
Group D: Chelated Vanadocene Complexes
VDacac Vanadocene acetylacetonato monotriflate ($Cp_2V(CH_3COCH_2COCH_3)(O_3SCF_3)$)
VDBPY Vanadocene bipyridino ditriflate ($CP_2V(C_{10}H_8N_2)(O_3SCF_3)_2$)
VDHfacac Vanadocene hexafluoro acetylacetonato monotriflate $Cp_2V(CF_3COCH_2COCF_3)(O_3SCF_3)$)
VDH Vanadocene acethydroxamato monotriflate ($Cp_2V(CH_3CON(O)H)(O_3SCF_3$)
VDPH Vanadocene N-phenyl benzohydroxamto monotriflate ($Cp_2V(C_6H_5CON(O)C_6H_5)(O_3SCF_3$)
Group E. Oxovanadium Compounds
[(VO(phen)]=(diaqua)(1,10-phenanthroline)oxovanadium (IV) sulfate;
[VO(phen)$_2$]=(aqua)bis(1,10-phenanthroline)oxovanadium (IV) sulfate;
[VO(Me$_2$-phen)]=(diaqua)(4,7-dimethyl-1,10-phenanthroline)oxovanadium (IV) sulfate;
[VO(Me$_2$-phen)$_2$]=(aqua)bis(4,7dimethyl-1,10-phenanthroline)oxovanadium (IV) sulfate;
[VO(Cl-phen)]=(diaqua)(5-chloro-1,10-phenanthroline) oxovanadium (IV) sulfate;
[VO(Cl-phen)$_2$]=(aqua)bis(5-chloro-1,10-phenanthroline) oxovanadium (IV) sulfate;
[VO(bipy)]=(diaqua)(2,2'-bipyridyl)oxovanadium (IV) sulfate;
[VO(bipy)$_2$]=(aqua)bis(2,2'-bipyridyl)oxovanadium (IV) sulfate;
[VO(Me$_2$-bipy)]=(diaqua)(4,4'-dimethyl-2,2'-bipyridyl) oxovanadium (IV) sulfate;
[(VO(Me$_2$-bipy)$_2$]=(aqua)bis(4,4'dimethyl-2,2'-bipyridyl) oxovanadium (IV) sulfate;
[VO(Br,OH-acph)$_2$]=bis(5'-bromo-2'-hydroxyacetophenone)oxovanadium (IV).

Unless otherwise indicated, the following abbreviations are used throughout the remainder of the disclosure:
Cp, cyclopentadienyl
Cp$^-$, cyclopentadienyl anion
acac, acetonylacetonate
Bpy, 2,2' Bipyridine
Hfacac, hexafluoroacetylacetonate
Cat, catecholate
Dtc, diethyl dithio carbamate
Phen, penanthroline
PH, N-phenyl benzohydroxamic acids
H, acetohydroxamic acid
OTf, trifluoromethane sulphonate
THF, tetrahydrofuran
DMSO, dimethyl sulfoxide CH$_3$CN, acetonitrile
CH$_2$Cl$_2$, dichloromethane
d-d, laportte spin forbidden transitions
LMCT, ligand to metal charge transfer transitions
p-p*, intraligand charge transfer transitions The present invention concerns vanadium compounds, and the finding that such compounds have potent and selective anti-mitotic activity, and are particularly active and stable agents for inhibiting angiogenesis. As such, these compounds are useful to treat or prevent disorders such as diabetic retinopathy, hemangiomas, cancers with abnormal blood vessel supply, restenosis following vascular injury, and the like.

Vanadium (IV) compounds for use in this invention are as shown in formula I and formula II:

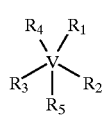

(I)

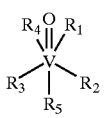

(II)

where R$_1$ and R$_2$ are each independently a monodentate ligand or together form a bidentate ligand; R$_3$ and R$_4$ are each independently a monodentate ligand or together form a bidentate ligand; and R$_5$ is a monodentate ligand, or is absent.

Suitable monodentate ligands include monodentate ligands are selected from the group consisting of halo, OH$_2$, O$_3$SCF$_3$, N$_3$, CN, OCN, SCN, SeCN, and a cyclopentadienyl ring, wherein each cyclopentadienyl ring is optionally substituted with one or more (C$_1$–C$_3$)alkyl. Suitable bidentate ligands are selected from the group consisting of acac, Bpy, Hfacac, Cat, Dtc, PH, H, and Phen, or derivatives thereof. The bidentate ligands may be substituted, for example, with one or more (C$_1$–C$_3$) alkyl, halo, (C$_1$–C$_3$) alkoxy, and halo (C$_1$–C$_3$) alkyl, and derivatives thereof. Halo is chloro, bromo, or iodo, and preferably is chloro.

In one embodiment, a useful vanadium compound has the following structure:

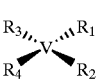

(III)

where R$_1$ and R$_2$ are each independently a monodentate ligand or together form a bidentate ligand; and R$_3$ and R$_4$ are each independently a cyclopentadienyl ring, wherein each cyclopentadienyl ring is optionally substituted with one or more (C$_1$–C$_3$)alkyl. In some preferred embodiments, R$_1$ and R$_2$ are each independently a monodentate ligand selected from the group consisting of of halo, OH$_2$, O$_3$SCF$_3$, N$_3$, CN, OCN, SCN, SeCN, and a cyclopentadienyl ring, where each cyclopentadienyl ring is optionally substituted with one or more (C$_1$–C$_3$)alkyl. Preferably, R$_1$ and R$_2$ are halo, and more preferably chloro. In some other embodiments, R$_1$ and R$_2$ together form a bidentate ligand selected from the group consisting of acac, Bpy, Hfacac, Cat, Dtc, PH, H, and Phen, or derivatives thereof. Preferably, the bidentate ligand is acac, or derivatives thereof.

Some specific examples of compounds of formula I are: VCp$_2$Cl$_2$ (VDC), VCp$_2$Br$_2$, VCp$_2$I$_2$, VCp$_2$(N$_3$)$_2$, VCp$_2$(CN)$_2$, VCp$_2$(NCO)$_2$, VCp$_2$(NCO)Cl, VCp$_2$NCS)$_2$, VCp$_2$NCSe)$_2$, VCp$_2$Cl(CH$_3$CN)(FeCl$_4$), VCp$_2$(O$_3$SCF$_3$)$_2$, V(MeCp)$_2$Cl$_2$, V(Me$_5$Cp)$_2$Cl$_2$, VCp$_2$(acac) (VDacac), VCp$_2$(hf-acac), VCp$_2$(bpy), VCp$_2$(cat), VCp$_2$(dtc), VCp$_2$PH, or VCp$_2$H. Two particularly useful vandocene compounds are VDC and VDacac.

Examples of useful oxovanadium compounds of formula II include the compound having the following structure:

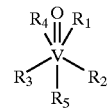

where R$_1$ and R$_2$ are each independently a monodentate ligand or together form a bidentate ligand; R$_3$ and R$_4$ together form a bidentate ligand; and R$_5$ is a monodentate ligand, or is absent. In some preferred embodiments, R$_1$ and R$_2$ are each independently a monodentate ligand selected from the group consisting of halo, OH$_2$, O$_3$SCF$_3$, N$_3$, CN, OCN, SCN, SeCN, and a cyclopentadienyl ring, wherein each cyclopentadienyl ring is optionally substituted with one or more (C$_1$–C3)alkyl, and R$_3$ and R$_4$ together form a bidentate ligand selected from the group consisting of acac, Bpy, Hfacac, Cat, Dtc, PH, H, and Phen, or derivatives thereof. In embodiments where R$_1$ and R$_2$ together form a bidentate ligand, the bidentate ligand is preferably selected from the group consisting of acac, Bpy, Hfacac, Cat, Dtc, PH, H, and Phen, or a derrivative thereof.

Specific compounds of formula II include [VO(phen)], [VO(phen)$_2$], [VO(Me$_2$-phen)], [VO(Me$_2$-phen)$_2$], [VO(Cl-phen)], [VO(Cl-phen)$_2$], [VO(bipy)], [VO(bipy)$_2$], [VO(Me$_2$-bipy)], [VO(Me$_2$-bipy)$_2$], and [VO(Br,OH-acph)$_2$].

The vandocene compounds can be used as anti-angiogenesis and anti-mitosis agents. In some embodiments, such compounds are used in the treatment of disorders in animals, and in particular in the treatment of diabetic retinopathy, hemangiomas, cancers with abnormal blood vessel supply, restenosis following vascular injury, and the like.

In such cases, the compounds both inhibit angiogenesis, and act as an anti-mitotic agent within the cells. In this manner the compounds of the present invention are acting in a dual function, to both reduce the blood supply and to disrupt mitosis in dividing cells.

Administration of the compounds as salts may be appropriate. Examples of acceptable salts include alkali metal (for example, sodium, potassium or lithium) or alkaline earth metal (for example calcium) salts, however, any salt that is non-toxic and effective when administered to the animal being treated is acceptable.

Acceptable salts may be obtained using standard procedures well known in the art, for example by reacting a sufficiently acidic compound with a suitable base affording a physiologically acceptable anion.

The compositions of the invention can be formulated as pharmaceutical compositions and administered to an animal host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained. When administered orally, the compositions of the invention can preferably be administered in a gelatin capsule.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any, unit dosage form should be pharmaceutically acceptable and substantially non-toxic in the amounts employed. In addition, the active compound may be incorporated into sustained-release preparations and devices.

The compositions of the invention may also be administered intravenously or intraperitoneally by infusion or injection. Solutions of the active composition can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active composition in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compositions may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pumptype or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compositions of the invention in a liquid composition, such as a lotion, will be from about 0.1–50 wt-%, preferably from about 0.5–5 wt%. The concentration in a semi-solid or solid composition such as a gel or a powder will be about 0.1–5 wt-%, preferably about,0.5–2.5wt-%.

The amount of the composition required for use in treatment will vary not only with the particular salt selected but also with the route of administration, the nature of the condition being treated, and the age and condition of the patient, and will ultimately be at the discretion of the attendant physician or clinician.

In general, however, a suitable dose will be in the range of from about 0.1 to about 150 mg/kg, e.g., from about 10 to about 75 mg/kg of body weight per day, such as 3 to about 50 mg per kilogram body weight of the recipient per day, preferably in the range of 1 to 100 mg/kg/day, most preferably in the range of 5 to 20 mg/kg/day.

The compositions are conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1–100 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Following i.m. administration, the compositions of the invention enter the blood stream within about 10–15 minutes and reach a maximum concentration in the blood within one hour of administration, at which point they can be found throughout the circulatory related organs.

Note, for the examples that follow, Tetraphenyl borate, trifluoromethanesulfonato and acetyl acetone were purchased from Aldrich Chemical Co. (Milwaukee, Wis.). Other reagents used were of commercially available reagent grade quality, and unless otherwise stated, all solvents were used as received from Aldrich (Sure Seal bottle, <0.005% water). Tetrahydrofuran was dried by distillation over sodium. Infrared spectral data were recorded using a FT-Nicolet model Protege 460 and taken as a KBr pellet. Frequencies were generally in the range of 4000–500 cm$^{-1}$. UV-Vis spectra were recorded in a quartz cell on a Beckmnan Model DU 7400 spectrophotometer and the spectral bands were registered in the the 250–800 nm range. Electron paramagnetic resonance (EPR) spectra were recorded in standard PBS buffer on a Bruker ESP 300 EPR spectrophotometer (9.64 GHz) using 4102 standard cavity. The g values were calibrated with a Varian strong pitch (0.1% in KCl) standard (g value 2.0028). The samples (in PBS) for EPR spectral analysis were studied in Willmad WG-814 standard TE$_{102}$ aqueous cell cavity (0.3 mm inner path length) to minimize the dielectric loss. Hyde, Rev Sci Instrum, 43: 629, 1972. Magnetic moments were determined by Evans method in CDCl$_3$ on a Varian 300 MHz FTNMR spectrometer. (Evans, *J Chem Soc*, 2003, 1959).

In some embodiments, the compounds of the invention can be administered before, during and/or after a vascular injury. Vascular injuries occur in human patients, for example, after medical procedures such as coronary angioplasty. These percutaneous procedures are conducted on patients with stable angina with single vessel disease, as well as those with multivessel disease, total occlusion, complex lesions, unstable angina and acute myocardial infarction. Several procedures in common use today can result in vessel injury, and would benefit from the method of the invention. These include balloon angioplasty, vessel stents, rotational and directional atherectomy, and laser angioplasty.

In a preferred embodiment, a patient is pretreated a vanadium compound such as VDacac at least one to three days before the treatment or procedure which is known to induce vascular injury. For example, it is preferred that administration of the vanadium compound is performed one to three days before a medical procedure such as PTCA. Delivery of the vanadium compound preferably continues after the vascular injury or medical procedure up to a period of about 2 weeks to 6 months post injury. The compound is preferably administered to the patient for a period of about 1 month to 3 months post injury. It is believed that the period 1 month to 3 months is the time at which restenosis formation peaks after a vascular injury.

However, often the pretreatment option is not available to patients in an emergency situation. An emergency situation may arise requiring a medical procedure that causes vascular injury. In that situation, the vanadium compound can be administered during the procedure and/or after the procedure. The compound can be administered for a period after injury of 2 weeks to about 6 months, preferably at least 1 to 3 months.

The administration of the vanadium compound ameliorates or prevents development of restenosis. Some level of neointima hyperplasia can still be present in those patients treated with vanadium compounds, but the formation of neointima is significantly ameliorated compared to untreated patients. Treatment course and dose of the vanadium compounds can be adjusted in the patient if the clinical signs indicate a need for increased dose or treatment time.

Methods for analysis of restenosis are known, and include, for example, quantitative coronary angiography (QCA), where narrowing of a vessel is visualized by injection of a visualizing dye. Another method for analyzing restenosis is by intravascular ultrasound imaging (IVUS). By inserting the ultrasound probe into a vessel, the diameter of the vessel, as well as the type and extent of lesions in the vessel can be analyzed.

EXAMPLES

The present invention may be better understood with reference to the accompanying examples that are intended for purposes of illustration only and should not be construed to limit the scope of the invention, as defined by the claims appended hereto.

Example 1
Synthesis of Vanadium Compounds

Vanadium compounds useful in the invention may be prepared by known methods, as described, for example, in published PCT Applications W099/36063; WO 00/27389; and WO 00/35930. For example, VDC (VCp$_2$Cl$_2$) and [VCp$_2$(acac)](CF$_3$SO$_3$); (VDacac) were prepared by following literature procedures (Wilkinson et al., *J. Am. Chem. Soc.*, 76: 42814284, 1954; Doyle et al., *Inorg. Chem.*, 7: 2479–2484, 1968) and purity was confirmed by $^1$H NMR, IR spectroscopy, and elemental analysis.

Example 2
Inhibition of Angiogenesis

The present example illustrates that vanadium compounds such as [VCp$_2$(acac)](CF$_3$SO$_3$) are effective inhibitors of angiogenesis.

Chick Embryo Chorioallantoic (CAM) Assay

Inhibition of embryonic angiogenesis was determined using a bioassay system involving CAMs of growing chick embryos, as previously described (Nguyen et al, *Microvascular Research*, 47:31, 1994; Auerbach et al, *Developmental Biology*, 41:391, 1974). Fertilized white Leghorn chicken eggs were received at day 3 of incubation from the University of Minnesota Poultry Research Center, St. Paul, Minn. The following procedures took place in a sterile laminar flow hood. The eggs were wiped down with 70% isoprpyl alcohol and allowed to air dry. The eggs were wiped with Betadine and placed in a horizontal position for approximately 5 minutes and allowed to dry. The eggs were cracked and placed into sterile 100×20 mm$^2$ Petri dishes (Fischer, Itasca, Ill.) and transferred to a 37° C. humidified incubator (1.5% $CO_2$). Pellets containing 1–100 µg [VCp$_2$(acac)](CF$_3$SO$_3$) in DMSO and 5% methylcellulose (Sigma, St. Louis, Mo.) were prepared by pipetting 10 µl of the compound, using a positive displacement pipette, onto sterile Teflon™ PFA Petri dishes (VWR, Chicago, Ill.) and drying in a vacuum desiccator at ambient temperature. The pellets containing the indicated dose of [VCp$_2$(acac)](CF$_3$SO$_3$) were implanted on the outer third of a 4–6 day old CAM surface, generally between two branches of a prominent blood vessel. The eggs were returned to a humidified 1.5% $CO_2$/37° C. incubator.

Inhibition of angiogenesis was assessed 48 hours after implantation by measuring the avascular one in the CAM beneath the pellet, followed by photographic documentation of the CAM. Pellets containing 200 µg suramin (Calbiochem, La Jolla, Calif.) served as a positive control. The methylcellulose disk alone with no added compounds served as a negative control. Significant inhibition of angiogenesis was defined as the presence of an avascular zone of at least 3 mm in diameter around the methylcellulose disk.

Results

The effect of [VCp$_2$(acac)](CF$_3$SO$_3$) on angiogenesis was examined in standard chorioallantoic membrane (CAM) assays using 4–6 day old chick embryos. [VCp$_2$(acac)](CF$_3$SO$_3$) in methylcellulose disks at doses ranging from 1 µg to 100 µg rapidly inhibited angiogenesis and produced within one hour a large avascular zone in the CAM around the methylcellulose disk, whereas control embryos implanted with empty discs did not develop avascular zones. The average size of the avascular zone increased with increasing dose of the vanadium compound.

The data indicates that the vanadium compound [VCp$_2$(acac)](CF$_3$SO$_3$) is a potent inhibitor of angiogenesis.

| VDacac (mg) | Avascular Zone (mm$^2$) |
| --- | --- |
| 1 | 7.0 ± 1.5 |
| 10 | 38.4 ± 16.6 |
| 100 | 92.4 ± 24.9 |

Example 3

Inhibition of Mitosis

This example illustrates that the vanadium compound [VCp$_2$(acac)](CF$_3$SO$_3$) is an effective inhibitor of embryonic development of Zebra fish, and in particular, is a potent inhibitor of mitosis.

Zebra Fish and Embryos

The adult wild type ZF were maintained generally according to the "Zebrafish Book" recommendations (Westerfield, *The Zebrafish Book*, 1993, 2d Edition Univ. of Oregon Press, Eugene). Males and females were kept in 10 Gallon tanks (70 fish per tank) with a constant slow flow of conditioned water at 26° C. and a controlled 14 hour day/10 hour night cycle. Adult fish were fed twice a day with live brine shrimp (Ocean Star International, Snowville, Utah) and each group of fish was bred once in two weeks. The embryos were obtained through (a) natural spawning at 28.5° C. in the breeding tanks with a netted false bottom or (b) fertilization in vitro using eggs and milt collected from the mature females and males anesthetized with Tricaine (Sigma, St.Louis, Mo.), as described (Westerfield, *The Zebrafish Book*, Supra).

Zebrafish Embryo Model System

ZF eggs were removed from their chorions by mild digestion in 1% Trypsin-EDTA (Sigma, St.Louis, Mo.) for 10 minutes at 28.5° C. (Standard temperature—ST), washed three times in "egg water" and twice in "embryonic medium" (EM), according to recommendations (Westerfield, *The Zebrafish Book*, Supra). The dechorionated two-cell stage cleaving eggs were transferred to the 24-well plastic cell culture plates (Costar, Cambridge, Mass.) filled with EM. Dechorionated embryos (10–12 per well) were exposed to the drugs at a constant ST for 0.5–24 hours. The final volume of the media in each well was 500 µL. The compound was tested at concentrations ranging from 10 µM to 4 mM. First dissolved in DMSO, it was then diluted serially with the incubation medium. The final concentration of DMSO in the wells was 1.2%. The sham-treated control embryos were incubated in EM in the presence of 1.2% DMSO.

Microinjections were performed with the help of a SMZ-10A stereo microscope (Nicon, Melville, N.Y.) and transjector 5246 (Eppendorf Scientific Inc, Westbury, N.Y. 11590) at RT. The eggs in chorions were restrained in agar grooves filled with EM, and the drug containing solution was introduced into the cytoplasm of one of the blastomeres of the two-cell stage eggs through a micropipette with a splinted sharp tip of 2–3 µm in diameter. All microinjections were performed under visual control. Drugs for injection were dissolved in Hank's Balanced Salt Saline (Gibco, Rockville, Md.) with 10% DMSO. The volume of the solution injected into each blastomere was approximately 2 µnl. For every drug, 40–50 embryos were injected in 30 minutes of one series of experiment. After the treatment the embryos were transferred back to ST and studied as above.

Observations of cell division and development of the ZF embryos were carried out using a SMZ-10A stereo microscope (Nicon, Melville, N.Y.), once every 30 minutes within the first 3 hours of incubation and at 6, 12 and 24 hours, as well. The drug effect was considered to be revealed when all embryos from one well were affected in a characteristic manner in 3 independent experiments. The stereo microscope was fitted with a specially designed transparent heating tray in order to keep embryos at ST during observations. Pictures of the embryos were taken with a H-III Photomicrographic System (Nicon, Melville, N.Y.) using Ektachrome 64X film (Kodak, Rochester, N.Y.). Cytotoxicity MTF Assays The cytotoxicity of [VCp$_2$(acac)](CF$_3$SO$_3$) against human cancer cell lines was performed as described previously (Ghosh et al, *Clinc Canc Res*, 6:1536, 2000) using the MTT (3-[4,5-dimethylthiazol-2-yl]-2,5-diphenyl tetrazolium bromide) assay (Boehringer Mannheim Corp., Indianapolis, Ind.). Briefly, exponentially growing tumor cells were seeded into a 96-well plate at a density of 2.5×10$^4$ cells/well and incubated [VCp$_2$(acac)](CF$_3$SO$_3$) or 0.1% DMSO in PBS concentrations ranging from 0.1 to 250 µM. Following incubation with drug for 48 hours at 37° C., to each well, 10 µl of MTT (0.5 mg/ml final concentration) was added and the plates were incubated at 37° C. for 4 hours to allow MTT to form formazan crystals by reacting with metabolically active cells. The formazan crystals were solubilized overnight at 37° C. in a solution containing 10% SDS in 0.01 M HCl. The absorbance of each well was measured in a microplate reader (Labsystems) at 540 nm and a reference wavelength of 690 nm. The percent survival and the IC$_{50}$ values were calculated using Graphpad Prism software version 2.0 (Graphpad Software, Inc., San Diego, Calif.), as described previously. Ghosh et al, Clinc Canc Res, 6:1536, 2000.

Immunocytochemistry and Confocal Microscopic Analysis

At the appropriate time points coverslips containing BT-20 cells were fixed in −20° C. methanol for 15 minutes followed by 15 minutes incubation in phosphate buffered saline +0.1% Triton X-100 (PBS-Tx). Coverslips were next incubated with a primary antibody recognizing α-tubulin (Sigma, St.Louis Mo.) for 40 minutes in a humidified chamber at 37° C. Coverslips were washed for 15 minutes in PBS-Tx followed by a 40 minutes incubation with a fluorescently labeled secondary antibody (Jackson Immunoresearch, West Grove, Pa.). The coverslips were again rinsed in PBS-Tx and incubated with 5 μM Toto-3 (Molecular Probes, Eugene Oreg.) for 20 minutes to label the DNA. Coverslips were immediately inverted onto slides in Vectashield (Vector Labs, Burlingame, N.H.) to prevent photobleaching, sealed with nail polish and stored at 4° C.

Slides were examined using a Bio-Rad MRC-1024 Laser Scanning Confocal Microscope mounted on a Nikon Eclipse E800 upright microscope with high numerical aperture objectives. Slides were examined to determine the percentage of cells in interphase vs. mitosis and representative images were taken. Digital data was processed using Lasersharp (Bio-Rad, Hercules, Calif.) and Photoshop (Adobe Systems, Mountain View, Calif.) software and printed on a Pictrography printer (Fuji Photo Elmsford, N.Y.)

Results

Embryonic development of the ZF (*Danio rerio*) is thoroughly studied and staged (Westerfield, *The Zebrafish Book*, 1993, 2d Edition (Univ. of Oregon Press, Eugene); Benyumov et al, *Rus. J. Dev. Biol.*, 26(2):132, 1995; Kimmel et al, *Dev. Dynam.*, 203:253, 1995). In a meroblastic egg, cell divisions are rapid and occur after the ooplasmic segregation on the animal pole of the egg cell, resulting within the first 3 hours of development in generation of a multicellular blastula comprised of several thousands of cells. The first series of cell divisions at the initial cleavage stage are approximately synchronous, only 15 minutes apart, and each set of the dividing blastomeres is characterized by a distinct pattern of cellular localization. This remarkable proliferation rate of undifferentiated eukaryotic vertebrate cells makes the ZF embryo an attractive experimental model for evaluation of new agents for anti-proliferative activity. In order to determine if the vanadium compounds such as [VCp$_2$(acac)](CF$_3$SO$_3$) could affect cell division, the effect on embryonic development of Zebra fish was examined.

As discussed above, the embryos were dechorionated with Trypsin-EDTA and incubated in embryonic medium containing either vehicle (1.2% DMSO) alone or vehicle with [VCp$_2$(acac)](CF$_3$SO$_3$) at different concentrations. At standard temperature of 28.5° C., two-cell stage control embryos exposed to the vehicle alone reached 4-cell, 8cell, and 64-cell stages within 15 minutes, 30 minutes, and 75 minutes, respectively. Within 3.5 hours post fertilization, these embryos developed into a high blastula and underwent gastrulation approximately 2.5 hours later.

[VCp$_2$(acac)](CF$_3$SO$_3$) inhibited cell division in a concentration-dependent fashion. At 0.6 mM, it caused cell division block at the 8–16 cell stage of embryonic development followed by total cell fusion and developmental arrest. At lower concentrations, cell proliferation continued but was abnormal. Specifically, within 120 minutes of incubation, cell division in the treated embryos was observed only on top of the blastodisc and whereas the cells on periphery and cells adjacent to the yolk were totally fused. The treated eggs did not form a compact blastoderm and developed no further.

The anti-proliferative effects of [VCp$_2$(acac)](CF$_3$SO$_3$) microinjected into the cytoplasm of two-cell'stage ZF eggs was next examine. At the lowest dose of 1 pmol/embryo, [VCp$_2$(acac)](CF$_3$SO$_3$) resulted in the formation of a blastocoel-like cavity in the blastoderm of late blastulae and early gastrulae and disrupted further gastrulation. At a dose of 40 pmols/cell, VDacac slowed down cell division and resulted in deterioration of the cell localization pattern and developmental block. Thus, vanadium compounds such as [VCp$_2$(acac)](CF$_3$SO$_3$) are a potent anti-mitotic agents.

The anti-mitotic effects of [VCp$_2$(acac)](CF$_3$SO$_3$) on proliferation of human cancer cell lines was examined using MTT assays. [VCp$_2$(acac)](CF$_3$SO$_3$) inhibited the proliferation of the breast cancer cell lines MDA-MB-231 and BT-20 as well as the glioblastoma cell line U373 in a concentration-dependent fashion with IC$_{50}$ values of 9.6 μM, 25.1 μM, and 35.7 μM, respectively.

The ability of [VCp$_2$(acac)](CF$_3$SO$_3$) to inhibit the proliferation of human cancer cells prompted the hypothesis that this compound likely affects mitotic spindle formation. To test this hypothesis, we examined the mitotic spindles of vehicle-treated and [VCp$_2$(acac)](CF$_3$SO$_3$)-treated BT-20 breast cancer cells using confocal laser scanning microscopy. Whereas in vehicle-treated control cells mitotic spindles were organized as a bipolar microtubule array and the DNA was organized on a metaphase plate, [VCp$_2$(acac)] (CF$_3$SO$_3$) -treated BT-20 cells had aberrant monopolar mitotic structures where microtubules were detected only on one side of the chromosomes and the chromosomes were arranged in a circular pattern. These results provide a cogent explanation for the anti-miotic activity of [VCp$_2$(acac)] (CF$_3$SO$_3$) against human cancer cells.

The data indicates that [VCp$_2$(acac)](CF$_3$SO$_3$) is a potent anti-proliferative agent, having disruptive effects on cell division during mitosis.

The above specification, examples and data provide a complete description of the manufacture and use of the composition of the invention. Since many embodiments of the invention can be made without departing from the spirit and scope of the invention, the invention resides in the claims hereinafter appended.

The above specification contains numerous references to literature and patent publications, each of which is hereby incorporated by reference as if fully set forth.

I claim:

1. A method for inhibiting angiogenesis in a non-cancerous tissue comprising administering to a subject in need of treatment an effective angiogenesis inhibiting amount of a vanadium compound having the following structure:

(III)

wherein
R$_1$ and R$_2$ are each independently a monodentate ligand or together form a bidentate ligand; and
R$_3$ and R$_4$ are each independently a cyclopentadienyl ring, wherein each cyclopentadienyl ring is optionally substituted with one or more (C$_1$–C$_3$)alkyl.

2. The method of claim 1, wherein R$_1$ and R$_2$ are each independently a monodentate ligand selected from the group consisting of halo, OH$_2$, O$_3$SCF$_3$, N$_3$, CN, OCN, SCN, SeCN, and a cyclopentadienyl ring, wherein each cyclopentadienyl ring is optionally substituted with one or more (C$_1$–C$_3$)alkyl.

3. The method of claim 2, wherein R$_1$ and R$_2$ are each independently halo.

4. The method of claim 3, wherein halo is chloro, bromo, or iodo.

5. The method of claim 3, wherein halo is chloro.

6. The method of claim 1, wherein R$_1$ and R$_2$ together form a bidentate ligand selected from the group consisting of acetonylacetonate, 2,2'bipyridine, hexafluoroacetylacetonate, catecholate, diethyl dithio carbamate, N-phenyl benzohydroxamic acids, acetohydroxamic acid and salts thereof.

7. The method of claim 6, wherein the bidentate ligand is acetonylacetonate or a salt thereof.

8. The method of claim 1 wherein the non-cancerous tissue is a vascular tissue.

9. The method of claim 8 wherein the vascular tissue is a coronary artery.

10. The method of claim 1 wherein the non-cancerous tissue is a retina.

11. The method of claim 1 wherein the non-cancerous tissue is a tumor.

12. The method of claim 11 wherein the tumor is a hemangioma.

13. The method of claim 8, where the angiogenesis is associated with injury to the vascular tissue.

14. The method of claim 13, wherein the angiogenesis is associated with restenosis following injury to the vascular tissue.

15. The method of claim 8, wherein the vascular tissue is a vessel.

16. The method of claim 15, wherein the vessel is a coronary artery.

17. The method of claim 15, wherein the injury to the vessel is associated with balloon angioplasty, vessel stent rotational and directional atherectomy, or laser angioplasty.

18. The method of claim 10, wherein the angiogenesis is associated with retinopathy.

19. The method of claim 18, wherein the retinopathy is associated with diabetes.

20. The method of claim 1, wherein said vandium compound is VC$_{p2}$Cl$_2$.

21. The method of claim 1, wherein said vandium compound is VC$_{p2}$Br$_{r2}$.

22. The method of claim 1, wherein said vandium compound is VC$_{p2}$I$_2$.

23. The method of claim 1, wherein said vandium compound is VC$_{p2}$(N$_3$)$_2$.

24. The method of claim 1, wherein said vandium compound is VC$_{p2}$(CN)$_2$.

25. The method of claim 1, wherein said vandium compound is VC$_{p2}$(NCO)$_2$.

26. The method of claim 1, wherein said vandium compound is VC$_{p2}$(NCO)Cl.

27. The method of claim 1, wherein said vandium compound is VC$_{p2}$(NCS)$_2$.

28. The method of claim 1, wherein said vandium compound is VC$_{p2}$(NCSe)$_2$.

29. The method of claim 1, wherein said vandium compound is [VC$_{p2}$Cl(CH$_3$CN)][FeCl$_4$].

30. The method of claim 1, wherein said vandium compound is VC$_{p2}$(O$_3$SCF$_3$)$_2$.

31. The method of claim 1, wherein said vandium compound is V(MeC$_p$)$_2$Cl$_2$.

32. The method of claim 1, wherein said vandium compound is V(Me$_5$C$_p$)$_2$Cl$_2$.

33. The method of claim 1, wherein said vandium compound is VC$_{p2}$(acac), wherein acac is acetonylacetonate.

34. The method of claim 1, wherein said vandium compound is VC$_{p2}$(hf-acac), wherein hf-acac is hexafluoroacetylacetonate.

35. The method of claim 1, wherein said vandium compound is VC$_{p2}$(bpy), wherein bpy is 2', 2' bipyridene.

36. The method of claim 1, wherein said vandium compound is VC$_{p2}$(cat), wherein cat is catecholate.

37. The method of claim 1, wherein said vandium compound is VC$_{p2}$(dtc), wherein dtc is diethyl dithio carbamate.

38. The method of claim 1, wherein said vandium compound is VC$_{p2}$(PH), wherein PH is a N-phenylbenzohydroxamic acid.

39. The method of claim 1, wherein said vandium compound is VC$_{p2}$(acethydroxamic acid).

* * * * *

UNITED STATES PATENT AND TRADEMARK OFFICE
CERTIFICATE OF CORRECTION

| | | |
|---|---|---|
| PATENT NO. | : 6,958,359 B1 | Page 1 of 3 |
| APPLICATION NO. | : 09/713780 | |
| DATED | : October 25, 2005 | |
| INVENTOR(S) | : Uckun | |

It is certified that error appears in the above-identified patent and that said Letters Patent is hereby corrected as shown below:

Title page, (56) References Cited, Other Publications, Vaitkus reference: "*Coron. Atery Dis.,*" should read --*Coron. Artery Dis.,*--

Col. 4, line 56: "acac, acetonylacetonate" should read --acac, acetylacetonate--

Col. 7, line 65: "and antifugal agents," should read --and antifungal agents,--

Col. 8, line 55: "about,0.5-2.5wt-%." should read --about 0.5-2.5wt-%.--

Col. 9, line 39: "mnan Model DU 7400" should read --man Model DU 7400--

Col. 11, line 8: "and 5% methylcellulose" should read --and 0.5% methylcellulose--

Col. 11, line 19: "avascular one in the CAM" should read --avascular zone in the CAM--

Col. 12, line 33: "approximately 2 µnl." should read --approximately 2 nl.--

Col. 12, lines 48-49: "Cytotoxicity MTF Assays" should read --Cytotoxicity MTT Assays--

Col. 12, lines 48-49: "Cytotoxicity MTT Assays" should start a new paragraph heading Col. 14, lines 5-6, "two-cell' stage ZF eggs was next examine." should read --two-cell stage ZF eggs was next examined.--

Col. 15, line 12, claim 6: "acetonylacetonate," should read --acetylacetonate,--

Col. 15, line 17, claim 7: "acetonylacetonate or a" should read --acetylacetonate or a--

Col. 16, lines 1-2, claim 20: "vandium compound is $VC_{P2}CI_2$." should read --vanadium compound is $VCp_2Cl_2$.--

Col. 16, lines 3-4, claim 21: "vandium compound is $VC_{P2}B_{r2}$." should read --vanadium compound is $VCp_2Br_2$.--

Col. 16, lines 5-6, claim 22: "vandium compound is $VC_{P2}I_2$." should read --vanadium compound is $VCp_2I_2$.--

UNITED STATES PATENT AND TRADEMARK OFFICE
CERTIFICATE OF CORRECTION

PATENT NO. : 6,958,359 B1
APPLICATION NO. : 09/713780
DATED : October 25, 2005
INVENTOR(S) : Uckun It is certified that error appears in the above-identified patent and that said Letters Patent is hereby corrected as shown below:

Col. 16, lines 7-8, claim 23: "vandium compound is $VC_{P2}(N_3)_2$." should read --vanadium compound is $VCp_2(N_3)_2$.--

Col. 16, lines 9-10, claim 24: "vandium compound is $VC_{P2}(CN)_2$." should read --vanadium compound is $VCp_2(CN)_2$.--

Col. 16, lines 11-12, claim 25: "vandium compound is $VC_{P2}(NCO)_2$." should read --vanadium compound is $VCp_2(NCO)_2$.--

Col. 16, lines 13-14, claim 26: "vandium compound is $VC_{P2}(NCO)Cl$." should read --vanadium compound is $VCp_2(NCO)Cl$.--

Col. 16, lines 15-16, claim 27: "vandium compound is $VC_{P2}(NCS)_2$." should read --vanadium compound is $VCp_2(NCS)_2$.--

Col. 16, lines 17-18, claim 28: "vandium compound is $VC_{P2}(NCSe)_2$." should read --vanadium compound is $VCp_2(NCSe)_2$.--

Col. 16, lines 19-20, claim 29: "vandium compound is $[VC_{P2}Cl(CH_3CN)][FeCl_4]$." should read --vanadium compound is $[VCp_2Cl(CH_3CN)][FeCl_4]$."

Col. 16, lines 21-22, claim 30: "vandium compound is $VC_{P2}(O_3SCF_3)_2$." should read --vanadium compound is $VCp_2(O_3SCF_3)_2$.--

Col. 16, lines 23-24, claim 31: "vandium compound is $V(MeC_p)_2Cl_2$." should read --vanadium compound is $V(MeCp)_2Cl_2$.--

Col. 16, lines 25-26, claim 32: "vandium compound is $V(Me_5C_p)_2Cl_2$." should read --vanadium compound is $V(Me_5Cp)_2Cl_2$.--

Col. 16, lines 27-28, claim 33: "vandium compound is $VC_{p2}(acac)$, wherein acac is acetonylacetonate." should read --vanadium compound is $VCp_2(acac)$, wherein acac is acetylacetonate.--

Col. 16, lines 29-30, claim 34: "vandium compound is $VC_{p2}(hf-acac)$," should read --vanadium compound is $VCp_2(hf-acac)$,--

Col. 16, lines 32-33, claim 35: "vandium compound is $VC_{p2}(bpy)$," should read --vanadium compound is $VCp_2(bpy)$,--

UNITED STATES PATENT AND TRADEMARK OFFICE
CERTIFICATE OF CORRECTION

PATENT NO. : 6,958,359 B1
APPLICATION NO. : 09/713780
DATED : October 25, 2005
INVENTOR(S) : Uckun It is certified that error appears in the above-identified patent and that said Letters Patent is hereby corrected as shown below:

Col. 16, lines 34-35, claim 36: "vandium compound is $VC_{p2}(cat)$," should read --vanadium compound is $VCp_2(cat)$,--

Col. 16, lines 36-37, claim 37: "vandium compound is $VC_{p2}(dtc)$," should read --vanadium compound is $VCp_2(dtc)$,--

Col. 16, lines 38-39, claim 38: "vandium compound is $VC_{p2}(PH)$," should read --vanadium compound is $VCp_2(PH)$,--

Col. 16, lines 41-42, claim 39: "vandium compound is $VC_{p2}(acethydroxamic\ acid)$." should read --vanadium compound is $VCp_2(acetohydroxamic\ acid)$.--

Signed and Sealed this

Fourteenth Day of November, 2006

JON W. DUDAS
*Director of the United States Patent and Trademark Office*